United States Patent [19]

Watanabe et al.

[11] Patent Number: 5,116,765

[45] Date of Patent: May 26, 1992

[54] METHOD FOR AUTOMATIC CHEMICAL ANALYZING

[75] Inventors: Haruhisa Watanabe; Satoshi Tanaka; Shinya Matsuyama, all of Tokyo, Japan

[73] Assignee: Olympus Optical Co., Ltd., Tokyo, Japan

[21] Appl. No.: 510,883

[22] Filed: Apr. 18, 1990

[30] Foreign Application Priority Data

Apr. 25, 1989 [JP] Japan ................................. 1-103457
Aug. 24, 1989 [JP] Japan ................................. 1-216111

[51] Int. Cl.⁵ .................. G01N 33/539; G01N 33/555
[52] U.S. Cl. ......................... 436/165; 356/39;
358/93; 364/413.07; 364/413.08; 436/63;
436/520; 436/534
[58] Field of Search .............. 356/39, 442; 358/93;
364/413.07, 413.08; 382/6; 436/63, 164, 165,
518, 805, 70, 167, 808, 809, 518-520, 534, 805,
807; 422/73

[56] References Cited

U.S. PATENT DOCUMENTS 4,794,450 12/1988 Saito et al. ....................... 358/93
4,839,681 6/1989 Hamano ........................... 354/286

OTHER PUBLICATIONS

Rinsho Kensa Koza 17, pp. 443-448 (Partial English Translation).

Primary Examiner—David L. Lacey
Assistant Examiner—David Redding
Attorney, Agent, or Firm—Stevens, Davis, Miller & Mosher

[57] ABSTRACT

A method for detecting and measuring the image of an agglutination particle pattern produced in a test liquid in which the existence of hemolysis in a test liquid is judged at the same time as an analysis is conducted of particle patterns produced in the test liquid in response to an immunological agglutination reaction. By this method, it is possible to increase the precision of the analysis of the particle pattern by feeding back the result of the judgement of the existence of hemolysis in the test liquid. A reaction apparatus suitable for use in the method according to the invention is also disclosed. In this apparatus, a plurality of wells for containing the test liquid are formed, and a plurality of marks are formed in positions where the marks can be read through the test liquid by an optical system for detecting the particle patterns produced in the test liquid. Therefore, hemolysis existing in the test liquid can be objectively judged.

3 Claims, 4 Drawing Sheets

Agglutination

Non-agglutination

Agglutination

Non-agglutination

FIG.3
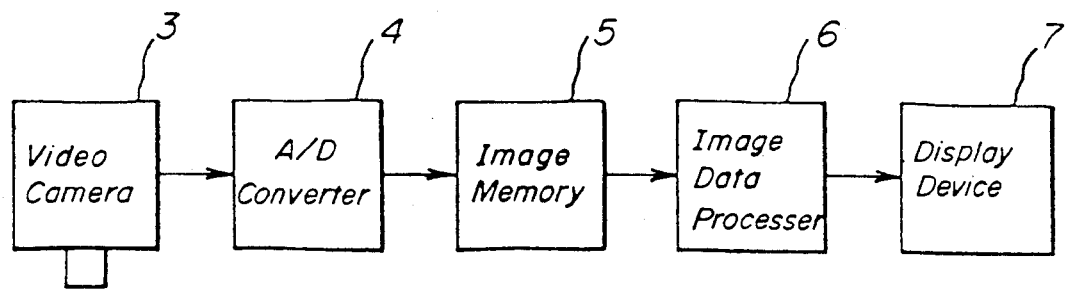
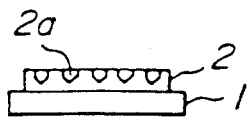
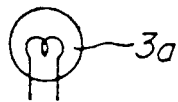
FIG.4
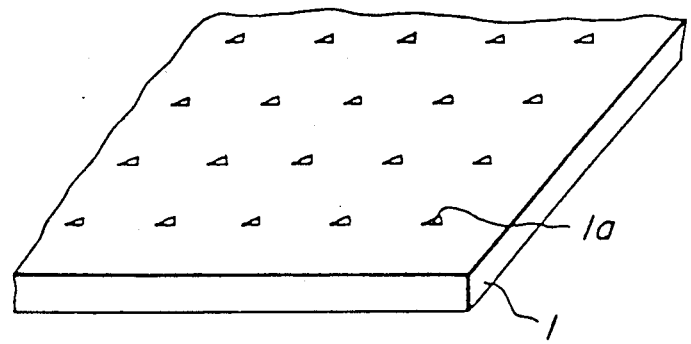

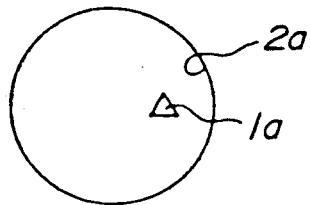
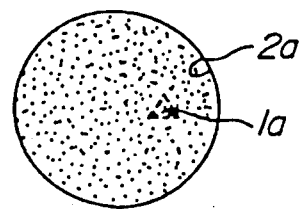
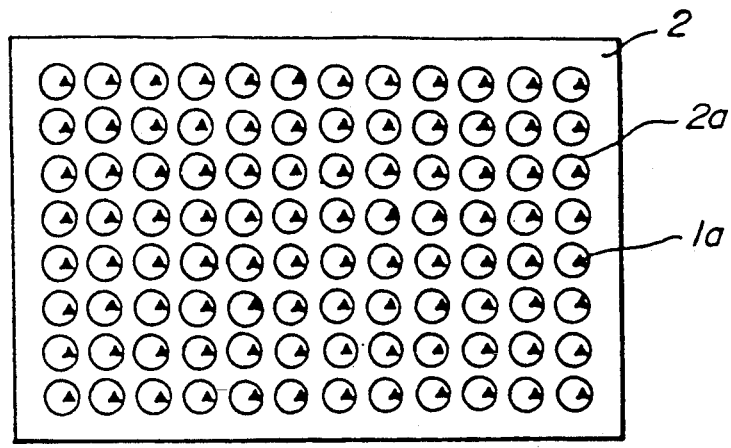
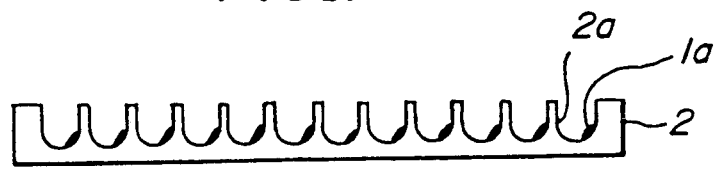

METHOD FOR AUTOMATIC CHEMICAL ANALYZING

BACKGROUND OF THE INVENTION

Field of the Invention and Related Art Statement

The present invention relates to a method for automatic chemical analyzing and a reaction apparatus therefor. Particularly, the method and apparatus according to the invention are suitably used for judging hemolysis existing in a test liquid as well as analyzing the agglutination patterns produced in the test liquid in response to an immunological agglutination reaction.

There are two types of methods used for judging the agglutination pattern produced in response to an immunological agglutination reaction. One of them is a sedimentation method. In the sedimentation method, a sample and a reagent are delivered into a reaction vessel having a conical bottom surface and then centrifuged. Thereafter the reaction vessel is kept at a standstill to form a particle pattern to be analyzed on the conical bottom of the reaction vessel. The other method is a shaking method, in which the sample and reagent are delivered into a reaction vessel having a wine-cup shaped bottom surface and then centrifuged. Thereafter the reaction vessel is shaken in order to judge whether an agglutination reaction has occured in the test liquid.

In the sedimentation method, when the immunological agglutination reaction occurs in the test liquid, the blood cell particles are spread over the conical bottom surface of the reaction vessel to form an agglutination pattern thereon. When the immunological agglutination reaction does not occur in the test liquid, the blood cell particles slip down along the inner surface of the reaction vessel and gather at the center of the bottom surface to form a non-agglutination pattern thereat. These patterns formed on the bottom surface of the reaction vessel are shown in FIGS. 1A and 1B. Contrary to this, in the shaking method, when the immunological agglutination reaction has occured in the test liquid, the blood cell particles gather at the center of the wine-cup shaped bottom surface of the reaction vessel. When the immunological agglutination reaction does not occur in the test liquid, the blood cell particles are diffused into the test liquid as a whole. FIGS. 2A and 2B are side views illustrating these particle patterns formed in the reaction vessel by the shaking method.

When the hemolysis exists in the test liquid, the higher the degree of hemolysis, the higher the transparency of the test liquid. The test, liquid, having hemolysis to a high degree becomes the color of red ink, and even when the reaction vessel containing the test liquid is shaken, the transparency thereof does not change. On the other hand, the lower the degree of hemolysis, the lower the transparency of the test liquid, so that an object placed beyond the reaction vessel could not be seen through the test liquid.

Therefore, if hemolysis is caused in the test liquid by destroying the blood cells contained in the sample or reagent, the agglutination or nonagglutination patterns thereof could not be analyzed correctly. That is to say, if hemolysis exists in the test liquid, there is a fear that the non-agglutination pattern will be judged as an agglutination pattern in the segmentation method, and the agglutination pattern will be judged as a non-agglutination pattern in the shaking method. Therefore, it is necessary to check the existence of hemolysis in the test liquid prior to analyzing the particle pattern formed in the test liquid in order to obtain correct analyzing results.

Hitherto, the judgement of hemolysis was visually conducted by an operator before automatically analyzing the particle pattern formed in the test liquid by an analyzing apparatus. However, since the hemolysis reaction is very sensitive, skilled operators and many hours are required for judging. The visual judgement of the hemolysis lowers the analyzing efficiency of the automatic analyzing apparatus, and the visual judgement over many hours is apt to cause mistakes which affect the final judgement of the agglutination reaction in the test liquid.

Furthermore, there has not been suggested a special reaction apparatus suitable for use in the judgement of hemolysis existing in the test liquid, and thus, prior to the present invention, it was impossible to automatically judge hemolysis in the test liquid in the conventional analyzing apparatus.

SUMMARY OF THE INVENTION

The present invention has for an object to provide a method for automatic chemical analyzing by it is possible to automatically objectively and correctly check whether hemolysis exists in the test liquid and to increase the precision of the final analyzing, such as analyzing the immunological agglutination reaction, by feeding back the result of the judgement of hemolysis to the analyzing result of the immunological agglutination reaction.

It is another object of the present invention to provide a novel reaction apparatus for use in the method according to the invention.

In order to carry out the first object of the invention, the method according to the present invention comprises the following steps:

picking up an image of a mark as well as an image of a particle pattern produced in a test liquid through the test liquid by an image pick up device;

processing the image of the mark picked up by said picking up device;

calculating a numerical value of a sharpness of the mark;

judging the existence of hemolysis in the test liquid from the numerical value to derive a hemolysis judgement signal; and managing a judgement of agglutination or nonagglutination in accordance with said hemolysis judgement signal.

According to the method of the invention, an image of a mark, as well as an image of a particle pattern formed in the reaction vessel, is picked up through the test liquid by the image pick up device; and a sharpness of the mark is compared with a given threshold value to judge the existence of hemolysis in the test liquid. Therefore, it is possible to objectively judge the existance of hemolysis in the test liquid using a machine with a high efficiency and without causing mistakes.

In order to carry out the second object of the invention, the reaction apparatus according to the invention comprises:

a plurality of wells for containing said test liquid; and a plurality of marks which are readable through the test liquid by an optical system for detecting particle patterns produced in said wells.

In the reaction apparatus of the invention, there are provided a plurality of marks which are readable through the test liquid by the optical system for detecting particle patterns formed in the test liquid. Therefore, by using the reaction apparatus according to the invention, the images of the marks as well as the images of the particle patterns can be picked up and thus the judgement of the existence of hemolysis existing in the test liquid can be easily conducted.

BRIEF DESCRIPTION OF THE DRAWINGS

FIG. 3 is a block diagram for explaining the method for judging the existence of hemolysis according to the invention;

FIG. 4 is a schematic view illustrating the base plate on which a plurality of marks for use in the judgemenet of hemolysis are formed;

FIG. 5A is a schematic plan view representing a reaction vessel in which hemolysis exists, and FIG. 5B is a schematic plan view representing the reaction vessel in which hemolysis does not exist;

FIG. 6 is a schematic plan view showing an embodiment of the reaction apparatus according to the invention;

FIG. 7 is a schematic side view depicting the microplate shown in FIG. 6; and

DETAILED DESCRIPTION OF THE PREFERRED EMBODIMENTS

Figure 1A:
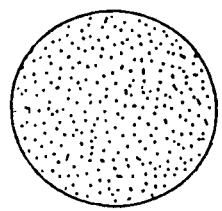
FIGS. 1A and 1B are schematic views showing particle patterns formed in the reaction vessels by the door sedimentation method.
Figure 1B:
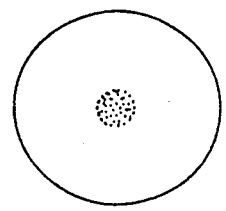
Figure 2A:
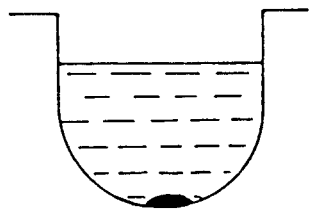
FIGS. 2A and 2B are schematic views depicting particle patterns formed in the reaction vessels by the shaking method.
Figure 2B:
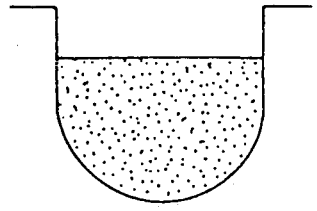

FIG. 3 is a block diagram explaining the method for judging hemolysis existing in the test liquid according to the invention.

In FIG. 3, the numerical number 1 denotes a base plate, 2 a microplate made of a transparent material having a plurality of wells 2a which are formed in a matrix manner on an upper surface of the microplate 2. FIG. 4 is a perspective view illustrating the base plate 1 on which the upper surface of which marks $\Delta 1a$ are formed in a matrix manner such that each mark 1a is situated under each well 2a formed in the microplate 2 and deviates from the center of each well 2a when the microplate 2 is put upon the base plate 1. After reagents and samples have been delivered into the wells 2a, the microplate 2 is put upon the base plate 1, and the image of particle patterns formed in each wells 2a in response to an immunological agglutination reaction as well as the images of the marks 1a are picked up by a video camera 3 which is arranged above the microplate 2. The numerical number 3a denotes a light source. Since the marks 1a exist under the bottom surfaces of the wells 2a, when hemolysis exists in the test liquid, the image of the mark 1a is clearly picked up by the video camera 3 as shown in FIG. 5A, because the test liquid becomes a transparent red color like red ink due to hemolysis. On the other hand, when there is no hemolysis in the test liquid, the image of the mark 1a is not picked up clearly or the image of the mark 1a could not be picked up at all by the video camera 3, as shown in FIG. 5B, because the test liquid becomes opaque.

After the picking up of the images of the particle patterns formed in the wells 2a and the marks 1a by the video camera 3, the output of the video camera 3 is supplied to an A/D converter 4 to be converted to digital image data, and then the digital image data are memorized in an image memory 5. Next, the digital image data of a data area of the mark 1a are processed in the following manner by image data processor 6.

The data processing conducted in the image data processor 6 is:

(1) Detecting an image of an edge of the mark 1a by processing the data area where the mark 1a exists;

(2) Calculating the degree of the sharpness of the edge detected in the process (1) numerically;

(3) Comparing the numerical value of the sharpness of the edge of the mark 1a with a given threshold value, and judging the existence of hemolysis in such manner that when the sharpness of the edge is higher than the threshold value, hemolysis exists in the test liquid, and when the sharpness of the edge is lower than the threshold value, there is no hemolysis in the test liquid.

The result of the data processing is displayed on a display device 7. After judging the existence of hemolysis, the test liquids having hemolysis are removed from the analyzing line and only the test liquids having no hemolysis are judged as to whether an agglutination particle pattern is formed or not.

According to the invention, the judgement of the existence of hemolysis in the test liquid can be automatically conducted by an analyzer. Therefore, it is possible to judge the existence of hemolysis speedy and correctly. Particularly in a big size analyzer in which a great number of samples are analyzed, it is possible to decrease the amount of labor required of the operator. Furthermore, by feeding back the result of the judgement of hemolysis to the analysis of immunological agglutination reaction, an increase in the preciseness of the agglutination analysis can be expected.

In the above mentioned embodiment, the marks 1a are formed on the upper surface of the base plate 1. Therefore, it is necessary to put the microplate upon the base plate 1 precisely.

FIGS. 6 and 7 are schematic plan and side views depicting an embodiment of the reaction apparatus according to the invention. As depicted in these figures, a plurality of wells 2a are formed in the microplate 2 in a matrix manner, and triangle shaped marks 1a are marked by painting or printing in the wells 2a so as to be deviated from the center of the bottom surface of the well.

According to the microplate shown in FIGS. 6 and 7, it is not necessary to put the microplate upon the base plate 1 precisely.

Figure 8:
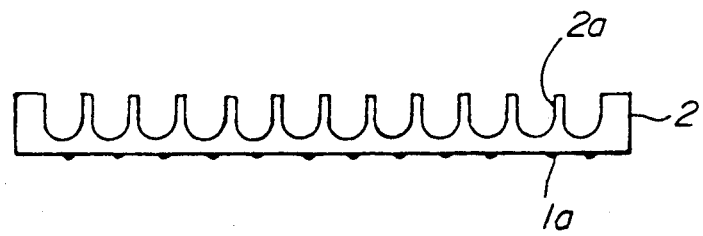
FIG. 8 is a schematic side view illustrating another embodiment of the reaction apparatus according to the invention.

FIG. 8 is a schematic side view representing a variation of the microplate shown in FIGS. 6 and 7. In this variation, each of the 1a is formed on the back surface of the microplate so as to deviate from the center of each well as viewed from the direction of the optical axis of the video camera 3. According to this microplate, when the wells 2a are washed to remove the test liquid contained therein after analyzing, the marks 1a do not easily disappear.

It should be noted that the shape of the mark does not matter to the effect of the invention and that the material of the microplate should be transparent or semitransparent. Further, in the embodiment mentioned in the above, the analyzing is conducted automatically by using an analyzer, but the method of the invention can be applied to the visual judgement of hemolysis.

What is claimed is:

1. A method for detecting and measuring the image of an agglutination particle pattern produced in a test liquid comprising:
   picking up an image of a mark as well as an image of a particle pattern produced in each one of a plurality of samples of a test liquid through the test liquid by an image pick up device;
   processing the image of each of the marks picked up from each sample by said pick up device;
   calculating a numerical value of the sharpness of each mark;
   judging the existence of hemolysis in each sample of the test liquid from the numerical value to derive a hemolysis judgement signal for each sample;
   removing any samples of the test liquid judged to have hemolysis;
   judging the remaining samples of the test liquid, which have no hemolysis, for the formation of an agglutination particle pattern; and
   feeding back the result of the judgement of hemolysis to the judgement of agglutination to increase the precision in analyzing the test liquid.

2. A method as claimed in claim 1, wherein:
   said marks are formed under each one of said plurality of samples of the test liquid contained in a plurality of reaction vessels so as to deviate from the lowest portion of a bottom surface of each one of said plurality of reaction vessels and the images of said particle patterns and said marks are picked up by the image pick up device arranged above said plurality of reaction vessels.

3. A method as claimed in claim 1, wherein:
   the step of judging the existence of hemolysis in each one of said plurality of samples of the test liquid comprises comparing the sharpness of each one of the marks formed under each one of said plurality of with a predetermined threshold value; wherein when the sharpness of the mark is higher than the threshold value, it is judged that hemolysis exists in the sample of the test liquid; and when the sharpness of the mark is lower than the threshold value, it is judged that hemolysis does not exist in the sample of the test liquid.

* * * * *